(12) United States Patent
Ou et al.

(10) Patent No.: US 10,688,497 B2
(45) Date of Patent: Jun. 23, 2020

(54) APPARATUS FOR THERMAL CONVECTION POLYMERASE CHAIN REACTION

(71) Applicant: Credo Biomedical Pte Ltd., Singapore (SG)

(72) Inventors: Yu-Cheng Ou, New Taipei (TW); Cheng-Yueh Chung, New Taipei (TW); Wei-Hao Liu, New Taipei (TW); Han-Yi Chen, New Taipei (TW)

(73) Assignee: Credo Diagnostics Biomedical Pte. Ltd., Singapore (SG)

( * ) Notice: Subject to any disclaimer, the term of this patent is extended or adjusted under 35 U.S.C. 154(b) by 275 days.

(21) Appl. No.: 15/698,625

(22) Filed: Sep. 7, 2017

(65) Prior Publication Data
US 2018/0221883 A1 Aug. 9, 2018

(30) Foreign Application Priority Data

Feb. 9, 2017 (CN) .......................... 2017 1 0070804

(51) Int. Cl.
*B01L 7/00* (2006.01)
*C12Q 1/686* (2018.01)
(Continued)

(52) U.S. Cl.
CPC ................. *B01L 7/52* (2013.01); *B01L 7/525* (2013.01); *C12Q 1/686* (2013.01); *C12Q 1/6844* (2013.01);
(Continued)

(58) Field of Classification Search
CPC .... B01L 7/52; B01L 7/525; B01L 2400/0445; B01L 2200/143; B01L 2200/16;
(Continued)

(56) References Cited

U.S. PATENT DOCUMENTS

| 2006/0068431 A1 | 3/2006 | Lee |
| 2013/0109021 A1 | 5/2013 | Hwang |
| 2016/0244810 A1 | 8/2016 | Su |

FOREIGN PATENT DOCUMENTS

| EP | 2 784 150 A1 | 10/2014 |
| JP | 2013-516976 A | 5/2013 |
| WO | 2005/100538 A1 | 10/2005 |

OTHER PUBLICATIONS

Shiyin Zhang et al., "A Convenient Nucleic Acid Test on the Basis of the Capillary Convective PCR for the On-Site Detection of Enterovirus 71", the Journal of Molecular Diagnostics, vol. 16, No. 4, Jul. 2014, pp. 452-458, XP055432034, Elsevier Inc.
(Continued)

*Primary Examiner* — Gautam Prakash
(74) *Attorney, Agent, or Firm* — Winston Hsu (57) ABSTRACT

The present invention discloses an apparatus for performing PCR by thermal convection. The device includes a first bracket, a second bracket, a temperature sensing device, a power supplying device, a processor and an accommodation space. The device uses transparent conductive film to replace conventional thermostat metal stock to perform a heat process required in the PCR or RT-PCR process. The device further uses a reagent container whose bottom portion contacts the transparent conductive film and being heated by the transparent conductive film to establish a thermal circulation in the reagent container. The device can qualify or quantify the product of PCR or RT-PCR process by further incorporating specific probes, fluorescence material, light source, light receiver and light regulator.

17 Claims, 3 Drawing Sheets

(51) Int. Cl.
*C12Q 1/6844* (2018.01)
*G01N 21/64* (2006.01)
*G01N 21/03* (2006.01)

(52) U.S. Cl.
CPC ....... G01N 21/645 (2013.01); G01N 21/6428 (2013.01); *B01L 2200/143* (2013.01); *B01L 2200/147* (2013.01); *B01L 2200/16* (2013.01); *B01L 2300/0654* (2013.01); *B01L 2300/18* (2013.01); *B01L 2300/1805* (2013.01); *B01L 2300/1827* (2013.01); *B01L 2400/0445* (2013.01); *G01N 21/0332* (2013.01)

(58) Field of Classification Search
CPC ......... B01L 2300/18; B01L 2300/1805; B01L 2200/147; B01L 2300/1827; B01L 2300/0654; G01N 21/645; G01N 21/6428; G01N 21/0332; C12Q 1/686; C12Q 1/6844; C12Q 2527/101; C12Q 2561/113; C12Q 2565/607; C12Q 2565/629

See application file for complete search history.

(56)  References Cited

OTHER PUBLICATIONS

Shiyin Zhang et al., "A one-step dipstick assay for the on-site detection of nucleic acid", Clinical Biochemistry, vol. 46, Issue 18, Dec. 2013, pp. 1852-1856, XP028797847, Elsevier Inc.

APPARATUS FOR THERMAL CONVECTION POLYMERASE CHAIN REACTION

BACKGROUND OF THE INVENTION

1. Field of the Invention

The present invention is related to a polymerase chain reaction (PCR) apparatus, and more particularly, to an apparatus containing a reagent container with its bottom portion being heated and top portion being heat dissipated to form a thermal convection, thereby establishing a temperature gradient which can therefore carry out the polymerase chain reaction.

2. Description of the Prior Art

Polymerase chain reaction (hereinafter referred to as "PCR") is a technology for rapid amplification of DNA, and its principle and the main steps include: (a) denature: using a relatively high temperature (90~95 Celsius degrees) for dissociating double-stranded DNA into single stranded DNA, which is then used as a template for replication; (b) primer annealing: when the temperature is lowered to a predetermined level, primers will be adhered to corresponding positions of the target genes; (c) primer extension: when the reaction temperature is about 72 Celsius degrees, by using magnesium ions as enzyme cofactors and DNA polymerase, the deoxy-ribonucleotide triphosphate (dNTP) will sequentially adhere after the primer and extended in accordance with the base sequence of the template, thus synthesizing a DNA fragment.

By repeating the three-step temperature increase/decrease process, the number of the target genes can be doubled in each repetition, thus can be $10^9$ times after 40 cycles of the three-step process. The signal of the target gene can therefore be greatly amplified. Accordingly, the PCR detection technology is generally used for detecting molecular signals in clinical diagnosis, such as pathogen diagnosis, diagnosis of genetic disease, diagnosis of cancer tumors, or the like. The RT-PCR technique which is derived from PCR also has similar principle and application, therefore is widely used in current techniques clinical diagnosis.

Devices used to perform PCR or RT-PCR reactions often include heat resistant plastics as the materials of the reaction tube. The amplification of nucleic acid is achieved by using the thermostat metal to repeatedly increase and decrease the temperature for the tube so as to reach different temperatures in each three-step process. In current system, the system with thermostat metal requires a relatively lager space, the entire temperature control system may occupy a larger space and has a large heat capacity ratio. In addition, according to current practice of operation, it requires 30-35 cycle and about two to three hours for one reaction, making it difficult to reduce the reaction time and hard to apply this technology to those reactions which require to obtain the results in a short time.

In order to improve the problems in conventional PCR machines, the researchers have developed the PCR and RT-PCR techniques by applying microfluidic chips technology. Microfluidic chip is characterized by adapting various conventional inspecting components, such as mixing reaction tank, heating reaction tank, separation pipe, and detection tank, etc., into the glass, the plastic, or silicon material by etching it to form the reaction tube and analyzing components in micro meter scale and by applying additional voltage to form a micro current, or by using micro-pump or centrifugal force, so as to drive the sample or the reagents flow between the micro-pipes so as to perform the inspection process. When there is fluorescent component or specific probe used in the reagent, the chip can further include a device for detecting the fluorescence to measure the quantity of target gene. Such integrally molded multi-functional chip is also known as "lab-on-a-chip." Since all the analysis are carried out in said micron pipelines, a very small amount of reagents and reactants is required for testing, and the analysis time can be relatively shortened due to the high heat transfer efficiency in comparison to conventional inspection machines. In current PCR or RT-PCR biochip, it usually includes a micro temperature sensor, a micro-heater and a micro-controller. Since the temperature sensor and the heater are integrated in the PCR or RT-PCR chip, the chip can quickly and more accurately perform the temperature control process, which have three steps: denaturing (around 90~95 Celsius degrees), primer adhering (50~65 Celsius degrees), and template extending (72 Celsius degrees), and the chip can adjust the circle numbers depending on the inspection requirement. The microfluidic chip technology, in comparison with traditional PCR or RT-PCR technique, is advantageous in that the volume of the microfluidic chip can reduce the overall heat capacity of the reagent or of the reactants, so the reaction time and reagent consumption can be reduced. However, it is still required for said chip to perform the heating and cooling temperature increasing/decreasing steps, so the time-consuming problem for carrying out these temperature oscillation steps can still not be avoided. So far, a type of micro-chips is developed, which excludes the uses of heaters to execute the repeated temperature increasing/decreasing steps. The chip uses special flow tubes or chambers to make the reactant/reagents repeatedly flow between three temperature zones so as to amplify the target genes. Although the use of such technique in PCR or RT-PCR process can exclude the time-consuming problem resulted from repeated heating and cooling processes, such technology requires complex system such as pressurized fluid systems and liquid driving systems. Because it is hard to predict the volume and the viscosity of the liquid, which is related to the liquid driving system, the system and the instruments with such technology become difficult to design and operate, indirectly limiting the development of such technology.

The researchers also develop another technology that uses thermal convection circulation to perform the PCR or RT-PCR reaction so the reagent and the reaction product can be in different temperatures at different locations, thereby solving the high-capacitance and time consuming problems in conventional arts. This technique uses of a high temperature heat source and a low temperature heat source, and by heating the upper and lower ends of the closed reaction tube which contains reagents and reactants, the liquid can be driven to flow through different temperature regions by the temperature difference between the two ends of the reaction tube, so as to carry out a PCR reaction. This technique, while overcoming the time consuming problem caused from repeated temperature increase/decrease steps, and also exclude external pressurization to drive the liquid flow cycle, however, still needs to avoid external temperature interference for its dual heat source, so the two heat sources requires a separate temperature control system (including a temperature sensor), and the processor should also be able to coordinate the temperatures at the two terminal ends to give desired reaction temperature for the primer adhesion. Thus, it requires a very complex mechanism to adjust such temperature, and since most of the heater is a massive metal, the volume of the machine as well as the heat capacity ratio cannot be reduced, resulting in a complex temperature control mechanism and metal heating system and high manufacturing costs. In view of the above problems, there is still a need in the art to develop a polymerase chain reaction apparatus which can solve the above-mentioned problems.

SUMMARY OF THE INVENTION

The present invention therefore provides a thermal convection PCR apparatus to solve the above-mentioned problems.

This device uses a glass coated by a transparent conductive material (also known as a transparent conductive film) as the heating means, and uses a temperature sensor disposed thereon for detecting the temperature of the heating means. After starting the device, the reagent container where the reactants and reagents are added is brought into contact with the heating means. The heat is conducted to the reagent container via the transparent conductive film. The liquid in the reagent container which is closer to the contact site starts to be heat first and by convection, the heat is gradually transferred to the liquid that is far from the contact site, so the temperature of the liquid far from the contact site becomes lower. By constant thermal convection, the liquid in the reagent container will exhibit a continuous temperature gradient distribution. When the contact portion of the reactants and the reagents is heated to 95 Celsius degrees, said portion will begin the denature step and by circulation of thermal convection inside the reagent vessel, the portion can start the step for primer annealing and primer extension steps. Thus, this apparatus can perform the PCR or RT-PCR reaction.

In order to ensure that the temperature cycle in the reagent container can process PCR or RT-PCR without being affected by the outside temperature, the present invention provides a semi-closed accommodation space for holding the reagent container. When the reagent container is placed into the accommodation space, the portion in which the reagent container is loaded is not exposed to the air, so when the device is in operation, the heat cycle of the reagent container is not affected by the change of the outside temperature. In other words, to ensure that the PCR or RT-PCR reactions is not affected by the outside temperature and there is sufficient temperature gradient in temperature inside the reagent container to form a heat cycle, the design of the accommodation space makes the top portion exposed to the outside temperature to dissipate the heat and keeps a temperature difference between the top portion of the accommodation space and the heat contact site to form a thermal convection circle within the reagent container. Once the circle reaches the reaction temperatures of the three cycling steps in PCR or RT-PCE, the accommodation can ensure the reaction not affected by the outside temperature, so the reaction can successfully proceed.

The present invention provides an apparatus with a reagent container for performing PCR or RT-PCR by thermal convection, and said reagent container has reactants and reagents, wherein the apparatus includes:

(1) a first bracket, disposed on a horizontal plane, wherein the first bracket includes a first perforation;
(2) a second bracket, disposed below the first bracket and substantially parallel to the horizontal plane, wherein the second bracket includes a second perforation, and the second bracket has a bracket upper surface and a bracket lower surface, wherein the bracket lower surface of the second bracket further includes a retaining groove, which is substantially parallel to the horizontal plane, wherein the retaining groove is connected to the second perforation;
(3) a temperature sensing device, disposed in the retaining groove, wherein the temperature sensing device includes a glass, a temperature sensor and a contact node, wherein the glass has a film upper surface and a film lower surface, and a transparent conductive film is disposed on the film upper surface or the film lower surface, the size of the glass is substantially equal to the size of the retaining groove such that the film upper surface or the film lower surface can be fixed in the retaining groove, and the contact node is disposed at the same side of the transparent conductive film, the temperature sensor can be disposed on the film upper surface or the film lower surface and is used to measure a temperature of the transparent conductive film;
(4) a power supplying device, including a power supply and a power regulator, wherein the power supply provides power to the contact nodes so the temperature sensing device can perform a heat process, and the power regulator is used to control an output current;
(5) a processor, for processing and regulating the power supply device; and
(6) an accommodation space, disposed between the first bracket and the second bracket and is used for accommodating the reagent container, wherein the reagent container is placed into the accommodation space through the first perforation and contacts the film upper surface of the glass further through the second perforation and the retaining groove, wherein the power supply supplies current to the contact nodes to heat up the glass, a temperature thereof is reported back to the processor by the temperature sensor, and the processor then controls the power regulator not to supply the current, then PCR starts to proceed.

Preferably, the apparatus is applied to PCR or RT-PCR.

Preferably, the transparent conductive film includes tin oxide, indium oxide, zinc oxide or indium tin oxide.

Preferably, the reagent container is fixed into the accommodation space at an angle substantially perpendicular along the first perforation, and contacts the film upper surface of the glass through the second perforation and the retaining groove.

Preferably, a number of the accommodation space is substantially equal to a number of the reagent container, and a top surface of the accommodation space in level with a top surface of the reagent in the reagent container, wherein the accommodation space is configured to avoid the reagent container from external temperature disturbance when PCR or RT-PCR is performed.

The present invention includes a temperature sensing device having a transparent conductive film, a temperature sensor and a contact node. The transparent conductive film is conductive and light transmissible, making it applicable to both flat panel display and architecture field. The transparent conductive film can be divided into metal film and metal oxide film, wherein the metal oxide film has good electrical conductivity and once being supplied to electrical power, it can be heat to a predetermined temperature in a very short time. The metal oxide therefore contains the advantage of fast heat capability, like metal, but can be alleviated from large volume consuming, which is the shortcoming of metal. The metal oxide is also featured by its transparency, making it more applicable to different fields. The metal oxide may refer to tin oxide, indium oxide, zinc oxide, or indium tin oxide, which is also used as the transparent conductive film in the present invention.

When there is fluorescent substance or specific probe added in the reagent, a light source and a light receiver can be included in the present to detect the generated fluorescence so the product of the reaction can be qualified, semi-quantified, or quantified. In one embodiment, the present invention provides an apparatus with a reagent container for performing PCR or RT-PCR by thermal convection, and said reagent container has reactants and reagents, said reagents include fluorescent material or probe, wherein the apparatus includes:

(1) a first bracket, disposed on a horizontal plane, wherein the first bracket includes a first perforation;

(2) a second bracket, disposed below the first bracket and substantially parallel to the horizontal plane, wherein the second bracket includes a second perforation, and the second bracket has a bracket upper surface and a bracket lower surface, wherein the bracket lower surface of the second bracket further includes a retaining groove, which is substantially parallel to the horizontal plane, and the retaining groove is connected to the second perforation;

(3) a temperature sensing device, disposed in the retaining groove, wherein the temperature sensing device includes a glass, a temperature sensor and a contact node, wherein the glass has an film upper surface and a film lower surface, and a transparent conductive film is disposed on the film upper surface or the film lower surface, the size of the glass is substantially equal to the size of the retaining groove such that the film upper surface or the film lower surface can be fixed in the retaining groove, and the contact node is disposed at the same side of the transparent conductive film, the temperature sensor can be disposed on the film upper surface or the film lower surface and is used to measure a temperature of the transparent conductive film;

(4) power supplying device, including a power supply and a power regulator, wherein the power supply provides power to the contact node so the temperature sensing device can perform a heat process, and the power regulator is used to control an output current;

(5) a light source, for excite the fluorescence material or the probe;

(6) a light receiver, for detecting or receiving fluorescence signal;

(7) a processor, for processing and regulating the power supply device; and (8) an accommodation space, disposed between the first bracket and the second bracket and is used for accommodating the reagent container, wherein the reagent container is placed into the accommodation space through the first perforation and contacts the film upper surface of the glass further through the second perforation and the retaining groove, wherein the power supply supplies current to the contact nodes to heat up the glass, a temperature thereof is reported back to the processor by the temperature sensor, and the processor then controls the power regulator not to supply the current, then PCR starts to proceed, next, after excited by the light source, the fluorescence material and the probe emits a light with a predetermined wavelength, the light will be detected by the light receiver, and the result thereof will be fed back to the processor.

Preferably, the apparatus may be applied to real-time PCR and real-time RT-PCR

Similar to the previous embodiment which does not include the fluorescence material, the specific probe, the light source and the light receiver, the light sensing device of this embodiment includes the transparent conductive film, the temperature sensor and the contact node, wherein the transparent conductive film includes tin oxide, indium oxide, zinc oxide or indium tin oxide for coating the glass.

The light source of the present invention can be an LED lamp, a laser light, or other light source that can emit light with wavelength that is consistent with that of the fluorescence material or the specific probe. The light receiver can contain a photodiode, a photomultiplier, a charge couple device (CCD) or a complementary metal-oxide-semiconductor (CMOS) or the like. When the PCR product is generated, it will be excited by the light with a predetermined wavelength from the light source to form fluorescence light with a predetermined wavelength, which will be captured by the light receiver. The device can therefore qualify, semi-qualify or quantify the concentration of the PCR product. When there are two or more than two types of fluorescence material or specific probes, the device can expand the number of the light receiver or the light sources, so as to detect two or more than two fluorescence signals. In the present invention, when the light source is direct below the second perforation, the light receiver can be located in the accommodation space and is substantially perpendicularly to the light source. When the light source is disposed in the accommodation space, the light receiver can be disposed below the second perforation and is substantially perpendicular to the light source. That is, the relative positions of the light source and the light receiver are not fixed to some decided locations. When the light source emits light from the side of the reagent container to excite the fluorescence material or the specific probe, the light receiver can be disposed at the bottom, the top or other locations of the reagent container that can be free from the disturbance of the light source. On the other hand, when the light source emits light from the bottom of the reagent container to excite the fluorescence material or the specific probe, the light receiver can be disposed at the top or other locations of the reagent container that can be free from the disturbance of the light source. In one preferred embodiment of the present invention, the direction of the light emit from the light receiver is substantially perpendicular to the detecting unit of the light source. The light source and the light receiver are disposed respectively at the bottom and the side of the reagent container, wherein the two components are perpendicular or about perpendicular to each other. By doing this, it is ensured that the light receiver can receive the light only from the light signal of the reagent container, rather than other light signal which is not from the reagent container and may influence the accuracy of the device.

Further, when the light source can emit multi-wavelength light (such as LED), a short wavelength light filtering material can be coated on the glass at the other side relatively to the transparent conductive film, so as to filter non-specific light source. By doing this, the light that cannot excite the fluorescence material or the specific probe can be filtered away, allowing only the light which can excite the fluorescence material or the specific probe passing through the transparent conductive film and the reagent container thereto precisely excite the fluorescence material or the specific probe. As a result, it is ensured that the light detected by the light receiver is truly the light emit from the PCR product.

Preferably, the reagent container is fixed into the accommodation space at an angle substantially perpendicular along the first perforation, and contacts the film upper surface of the glass through the second perforation and the retaining groove.

Preferably, a number of the accommodation space is substantially equal to a number of the reagent container, and a top surface of the accommodation space in level with a top surface of the reagent in the reagent container, wherein the accommodation space is configured to avoid the reagent container from external temperature disturbance when PCR or RT-PCR is performed. In the present invention, when the reagent container with reagent and reactants is contacting the heated transparent conductive film, the temperature of the liquid in the contact portion starts to rise, and the thermal circulation occurs in the entire reagent container by the effect of thermal convection. When the transparent conductive film reaches a predetermined value, the condition is detected by the temperature sensor and the power of the heater is then lowered, so the transparent conductive film is not heat and the temperature thereof can be kept in a suitable level. On the other hand, when the transparent conductive film is lowered than a predetermined value, the power of the heater will be boosted by the temperature sensor, making the temperature of the transparent conductive film rise to a predetermined value to ensure the reaction of PCR. When the PCR starts to generate its product, the light from the light source can excite the product through the transparent conductive film to emit fluorescence, and the fluorescence will be captured by the light receiver. Besides, the contact node is used to transmit current for the power supplier and the position of the contact node is located at the same side regarding to the transparent conductive film.

The present invention uses the transparent conductive film, instead of the conventional heater, to scale down the entire device. The present invention also uses the thermal convection theory to achieve the PCR reaction temperature, thus prohibit the time consuming problem resulted from repeated temperature increasing/decreasing process in conventional arts. Consequently, the entire reaction time can be saved and it is achievable to qualify or quantify the target gene in a short time.

These and other objectives of the present invention will no doubt become obvious to those of ordinary skill in the art after reading the following detailed description of the preferred embodiment that is illustrated in the various figures and drawings.

DETAILED DESCRIPTION

In achieving the above-mentioned objective, the present invention provides two preferred embodiments in the following context. The description, in combination with the figures, will explain structure and the effect of the preferred embodiment. In addition, the terms "before", "after", "right", "left", "up", "down" are used to describe the positions of the structures or the components, so as to correspond the space relationship when the user operates the preferred embodiment of the present invention.

The following embedment will take PCR as an example, but one skill in the art can realize to modify the parameters such as temperature thereto meet the process in operating RT-PCR.

Figure 1:
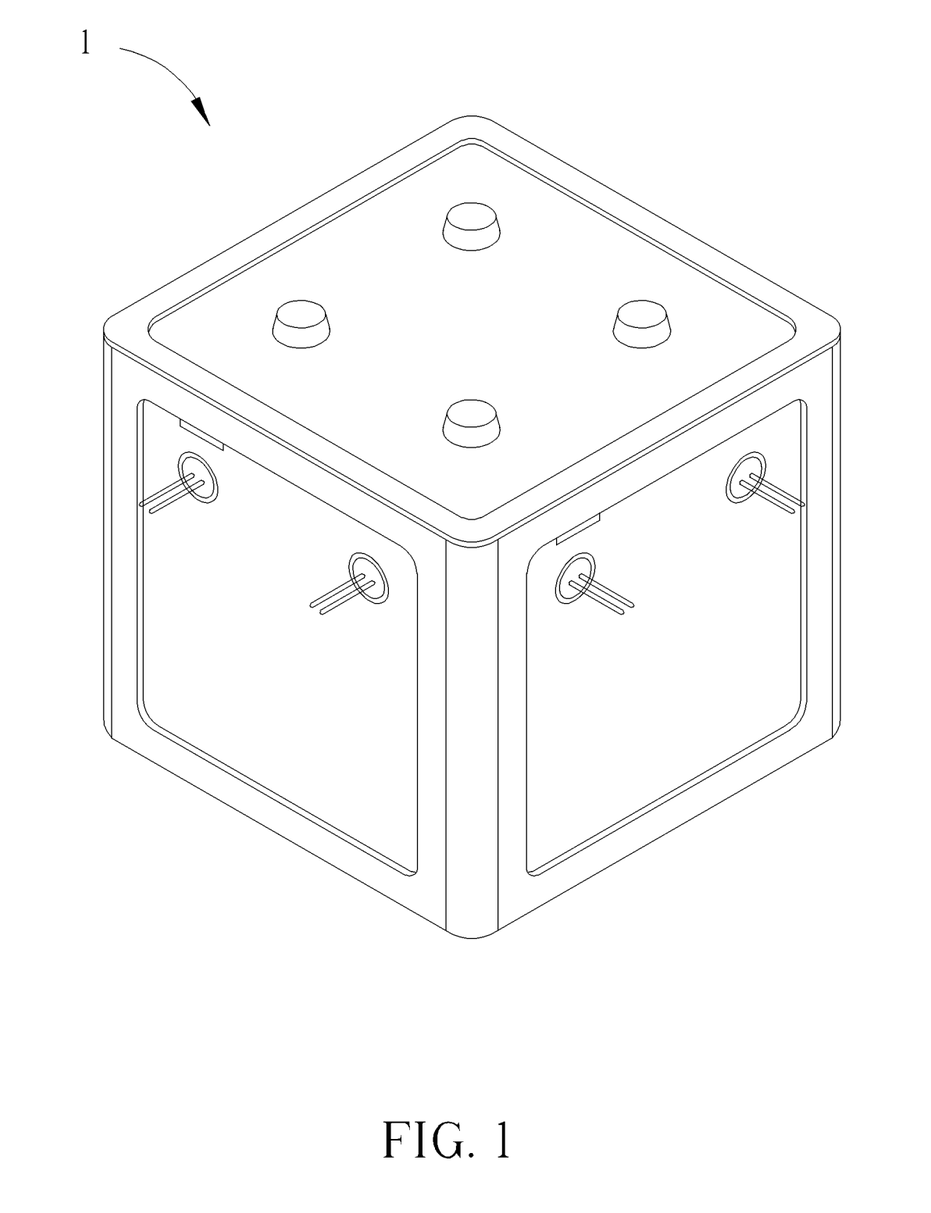
FIG. 1 is a schematic diagram of the appearance of the device.

Please refer to FIG. 1, which shows the appearance of the thermal convection PCR apparatus 1. Please also refer to FIG. 2 and FIG. 3. The device 1 in the preferred embodiment includes a first bracket 10, a second bracket 20 and an accommodation space 30. The first bracket 10 has a first perforation 101 for installing a test tube (or called "reagent container") 102 that contains reagent and reactant. The second bracket 20 has a second perforation 201 and a retaining groove 202. The second perforation 201 allows the test tube 102 to insert therein and fixes the test tube 102 into the retaining groove 202. The retaining groove 202 can also be used to accommodate a transparent conductive film 50. The accommodation space 30 is compartmented from every side, and the first perforation 101 and the second perforation 102 are respectively disposed above and below the accommodation space 30. When the test tube 102 is placed into the device 1, the top portion of the test tube 102 is exposed, and the heat can be dissipated therefrom. The bottom portion of the test tube 102 contacts the film upper surface 501 of the transparent conductive film 50 and is fixed thereby. The accommodation space 30 therefore becomes closed and the portion of the test tube 102 inserted into the accommodation space 30 is not exposed.

Figure 4:
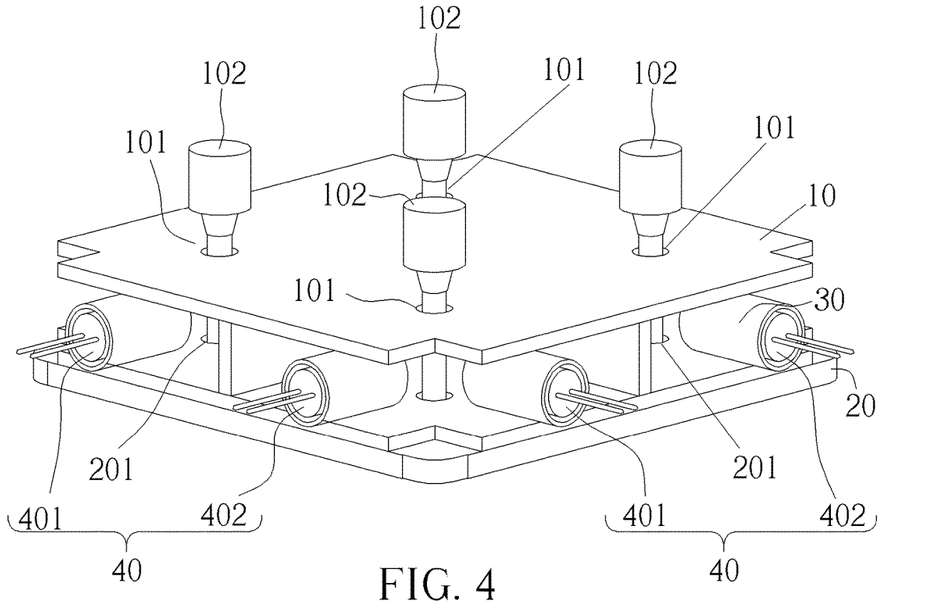
FIG. 4 is a schematic diagram of the photo-diode that can receive two lights with different wavelengths.

Please refer to FIG. 4. In this embodiment, the light receiver is a photodiode 40, and there are two photodiodes, the first photodiode 401 and the second photodiode 402, used to detect different light wavelengths of fluorescence. The first photodiode 401 and the second photodiode 402 are respectively disposed at the sides of the test tube 102 and the direction it emits the light is substantially perpendicular to the test tube 102, ensuring the light captured by the light photodiodes 401, 402 is not from the reflection of the test tube 102.

Figure 5:
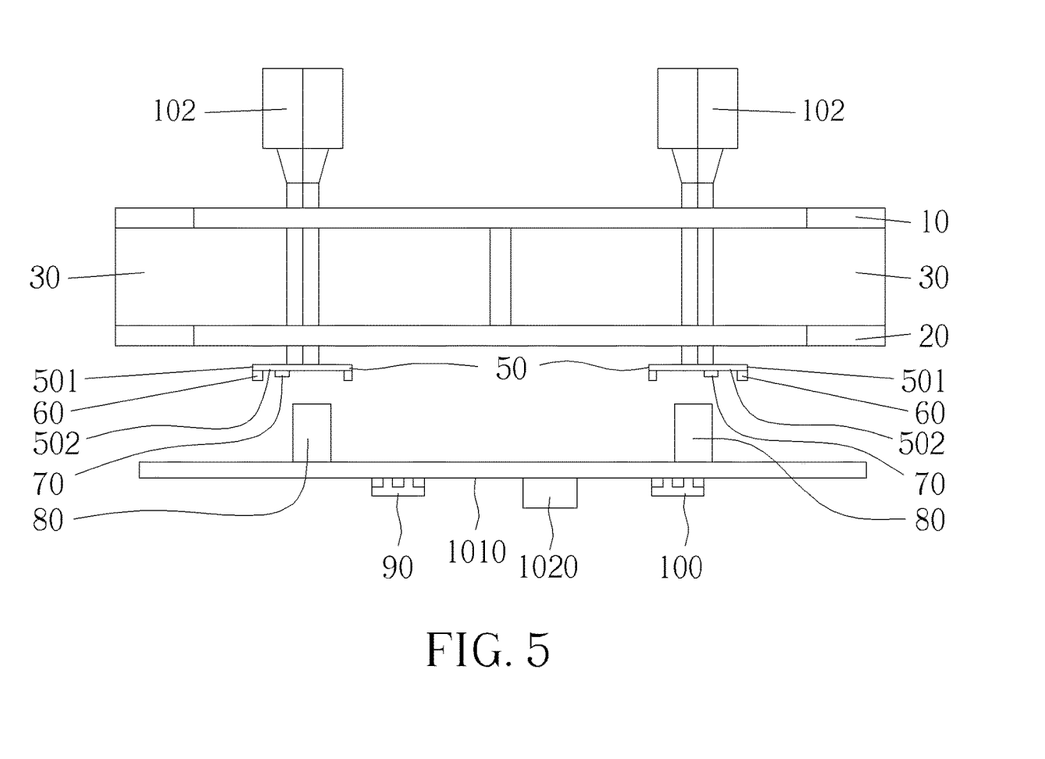
FIG. 5 is a schematic diagram of the device.

Please refer to FIG. 5. The present invention includes a third bracket 1010, a power supply 1020, a light source 80, a light source regulator 90, a processor 100 and a temperature sensing device including the transparent conductive film 50, the contact node 60 and the temperature sensor 70. The third bracket 1010 is configured to fix the light source 80, the light source regulator 90 and the processor 100. The light source 80 is configured to emit the light that can excite the fluorescence material or the specific probe. In the present embodiment, LED is used as the light source 80 and it is adjusted by the light source regulator 90. The light source regulator 1020 and the processor 100 are also placed onto the third bracket 1010, wherein the processor 100 is used to receive the signals form the light source regulator 90 and the temperature sensor 70 and can perform a control process. The processor 100 also can receive the signals from the first photodiode 401 and the second photodiode 402 and can analyze the signals. The power supplier 1020 is used to supply the power required to the device 1.

In the present embodiment, the temperature sensing device including the transparent conductive film 50, the contact node 60 and the temperature sensor 70 can provide heat for the test tube 102 so the reactant and the reagent in the test tube 102 can perform PCR process when it reaches an appropriate temperature. The transparent conductive film 50 such as indium tin oxide is coated on the film lower surface 502, and in improving the excitation of the fluorescence material and the specific probe, a short wavelength filter material is coated on the bracket upper surface 501 to filter the non-specific wavelength light form the light source 80. Besides, the size of the transparent conductive film 50 is substantially the same as that of the retaining groove 202 for accommodating the transparent conductive film 50. The contact node 60 and the transparent conductive film 50 is disposed at the film lower surface 502, configured to receive the current form the power supplier 1020 and conduct a heat function by using the received current. The temperature sensor 70 is disposed at the film lower surface 502, used to measure the temperature of the transparent conductive film 50 and then report it to the processor 100.

Figure 2:
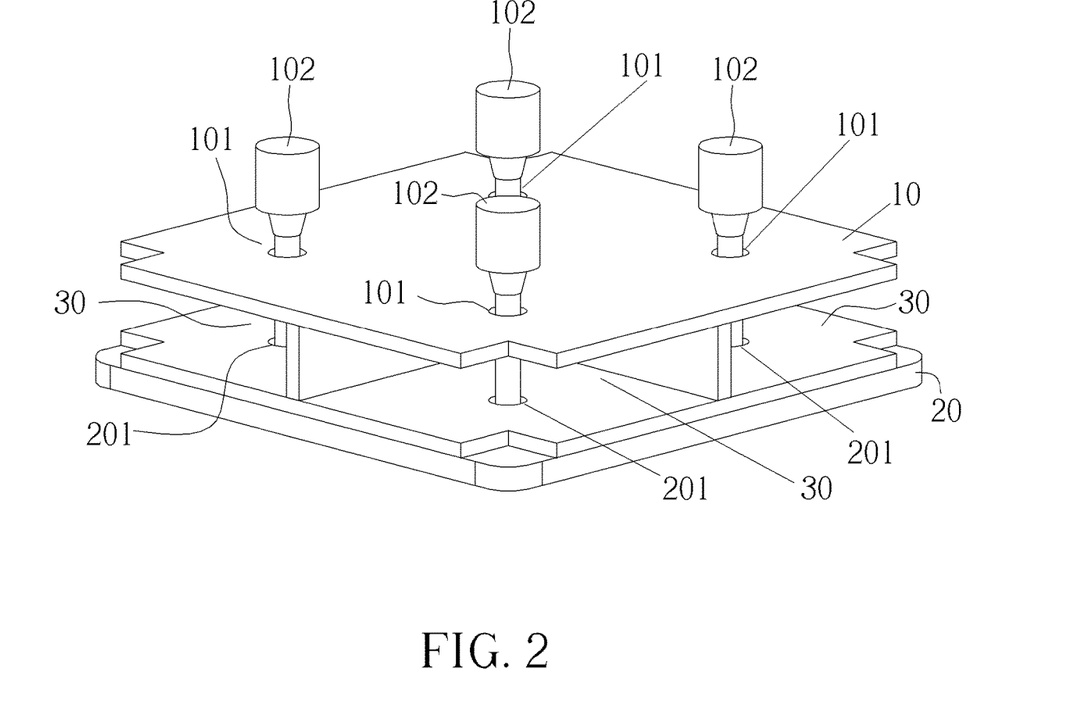
FIG. 2 is a schematic diagram of the relative positions of the bracket, the perforation and the reagent container.

When the device 1 starts to proceed, the test tube 102 containing the reagent and the reactant is placed into the first perforation 101 of the first bracket 10 and further into the second perforation 201 of the second bracket 20 to be fixed therein. The top surface of liquid in the test tube 102 is preferably level with a top surface of the accommodation space 30, so the accommodation space 30 becomes closed, and the bottom portion of the test tube 102 can directly contact the film upper surface 501 of the transparent conductive film 501 through the retaining groove 202. The power supplier 1020 supplies the current to the transparent conductive film 50 through the contact node 60 to perform a heat process. Since the bottom portion of the test tube 102 directly contacts the film upper surface 501 of the transparent conductive film 50, the heat will be transferred to the bottom portion of the test tube 102 by thermal convection from the transparent conductive film 50, thereby together heating the reagent and the reactants in the test tube 102. After a period time of heating, there will be a temperature gap between the top of the test tube 102 and the bottom portion of the test tube 102 that contacts the transparent conductive film 50, establishing a thermal circulation within the test tube 102. The thermal circulation in the test tube 102 is not affected by the outer environment and the temperature is maintained in the predetermined interval. The upper portion of the test tube not contained by the accommodation space 30 is exposed to the atmosphere to dissipate heat, and once the thermal circulation in the test tube 102 reaches the temperatures of three steps for carrying out PCR, the PCR reaction will soon be performed.

Right after the PCR reaction starts, the light regulator 90 on the third bracket 1010 turns on the light source 80 and it emits light through the film lower surface 502 of the transparent conductive film 50, wherein the light with non-specific wavelength is absorbed or filter away by the short wavelength filter material coated on the film upper surface 501 of the transparent conductive film 50, leaving the light with specific wavelength passing through the transparent conductive film 50 and therefore excites the two types of specific probes in the test tube 102. When the fluorescence is emitted, it will be detected by the first photodiode 401 and the second photodiode 402 respectively, and the detected signals will be transmitted to the processor 100 to analyze.

When the reaction is preceded, if the temperature sensor 70 detects that the reaction temperature is higher than the predetermined value, the condition will be feedback to the processor 100, and the processor 100 will notify the power supplier 1020 to stop the power for the transparent conductive film 50. Thus, the temperature of the transparent conductive film 50 will not rise anymore. On the contrary, when the reaction temperature detected by the temperature sensor 70 is lower than the predetermined value, the condition will be feedback to the processor 100 and the processor 100 will make the power supplier 1020 give more power, so the temperature of the transparent conductive film 50 would rise to the predetermined value. When the PCR reaction is finished, the processor 100 would control the light source regulator 90 to turn off the light 80 and further control the power supplier 1020 to stop supplying power to the contact node 60, thus stopping heating the transparent conductive film 50. The processor 100 will collect and analyze all the signals from the first photodiode 401 and the second photodiode 402 and report the result.

Figure 3:
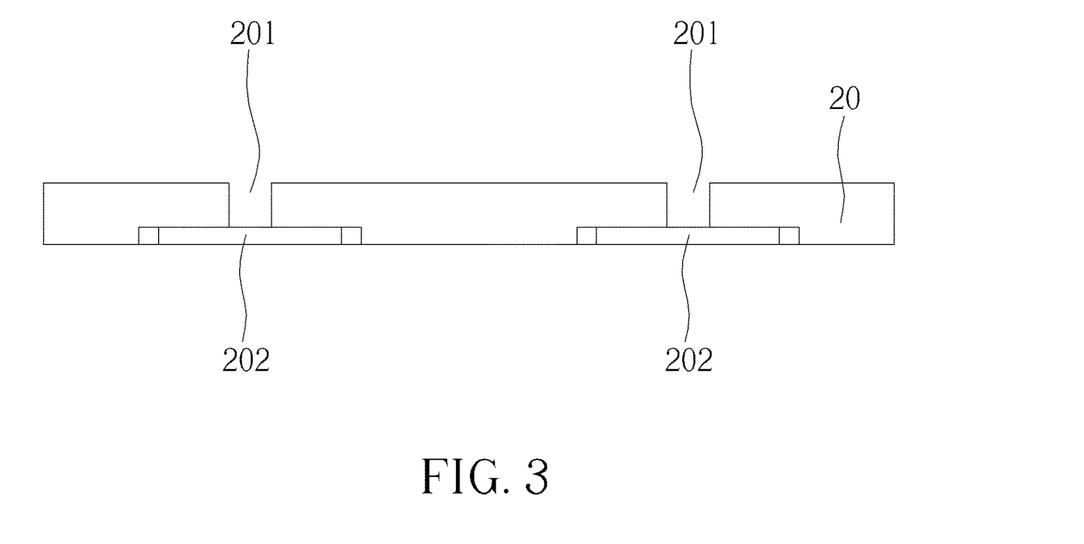
FIG. 3 is a schematic diagram showing the cross-sectional view of the retaining groove.

In another embodiment, the device disclosed by the present invention can also be applied to the PCR reaction that does not use fluorescence material or non-specific probes. The device 1 in this embodiment is similar to the previous embodiment, as shown in FIG. 1, FIG. 2 and FIG. 5. This embodiment can omit the first photodiode 401 and the second photodiode 402 as shown in FIG. 3, and the light source 80 and the light source regulator 90 in FIG. 5.

When the device 1 starts to proceed, the test tube 102 containing the reagent and the reactant is placed into the first perforation 101 of the first bracket 10 and further into the second perforation 201 of the second bracket 20 to be fixed therein. The height of the liquid surface in the test tube 102 is preferably level with a height of the accommodation space 30, so the accommodation space 30 becomes closed, and the bottom portion of the test tube 102 can directly contact the film upper surface 501 of the transparent conductive film 501 through the retaining groove 202. The power supplier 1020 supplies the current to the transparent conductive film 50 through the contact node 60 to perform a heat process. Since the bottom portion of the test tube 102 directly contacts the film upper surface 501 of the transparent conductive film 50, the heat will be transferred to the bottom portion of the test tube by thermal convection from the transparent conductive film 50, thereby together heating the reagent and the reactants in the test tube 102. After a period time of heating, there will be a temperature gap between the top of the test tube 102 and the bottom portion of the test tube 102 that contacts the transparent conductive film 50, forming a thermal circulation within the test tube 102. The thermal circulation in the test tube 102 is not affected by the outer environment and the temperature is maintained in the predetermined interval. The upper portion of the test tube not contained in the accommodation space 30 is exposed to the atmosphere to dissipate heat, and once the thermal circulation in the test tube 102 reaches the temperatures of three steps for carrying out PCR, the PCR reaction will soon be performed. When the reaction is finished, appropriate method can be performed to detect the results.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An apparatus with a reagent container for performing polymerase chain reaction (PCR) or reverse transcriptase polymerase chain reaction (RT-PCR) by thermal convection, and said reagent container comprises reactants and reagents, said reagents comprises a fluorescent material or a probe, wherein the apparatus comprises:
   (1) a first bracket, disposed on a horizontal plane, wherein the first bracket comprises a first perforation;
   (2) a second bracket, disposed below the first bracket and substantially parallel to the horizontal plane, wherein the second bracket comprises a second perforation, and the second bracket has a bracket upper surface and a bracket lower surface, wherein the bracket lower surface of the second bracket further comprises a retaining groove, the retaining groove is substantially parallel to the horizontal plane and connects the second perforation;

(3) a temperature sensing device, disposed in the retaining groove, wherein the temperature sensing device comprises a glass, a temperature sensor and a contact node, wherein the glass has a film upper surface and a film lower surface, and a transparent conductive film is disposed on the film upper surface or the film lower surface, the size of the glass is substantially equal to the size of the retaining groove so the glass can be fixed into the retaining groove by the film upper surface or the film lower surface, the contact node is disposed at the same side of the transparent conductive film, the temperature sensor is disposed on the film upper surface or the film lower surface and is configured to measure the temperature of the transparent conductive film;

(4) a power supplying device, comprising a power supply and a power regulator, wherein the power supply supplies power to the contact node so the temperature sensing device can perform a heat process, and the power regulator is configured to control an output current;

(5) a light source, configured to excite the fluorescence material or the probe;

(6) a light receiver, configured to detect or receive a fluorescence signal;

(7) an accommodation space, disposed between the first bracket and the second bracket and is configured to accommodate the reagent container, wherein the reagent container is placed into the accommodation space through the first perforation and further through the second perforation and the retaining groove to contact the film upper surface of the glass; and (8) a processor, for controlling the power regulator, and receiving signals from the temperature sensor and a light source regulator to control the temperature sensor and the light source, wherein, when the transparent conductive film reaches a predetermined value, a temperature of the transparent conductive film is reported back to the processor by the temperature sensor, and the processer controls the power regulator not to supply the power.

2. The apparatus according to claim 1, wherein the apparatus is applied to real-time PCR or real-time RT-PCR.

3. The apparatus according to claim 1, wherein the light receiver comprises a photodiode, a photomultiplier, a charge couple device (CCD) or a complementary metal-oxide-semiconductor (CMOS).

4. The apparatus according to claim 1, wherein the light source comprises a light-emitting diode (LED) or a laser.

5. The apparatus according to claim 1, wherein the light receiver and the light source are perpendicular to each other.

6. The apparatus according to claim 1, wherein the light source regulator, configured to control the switch of the light source.

7. The apparatus according to claim 5, wherein the light source is directly below the second perforation and the light receiver is disposed in the accommodation space and is perpendicular to the light source.

8. The apparatus according to claim 5, wherein the light source is disposed in the accommodation space and the light receiver is disposed below the second perforation and is perpendicular to the light source.

9. The apparatus according to claim 1, wherein the transparent conductive film is coated with the group of tin oxide, indium oxide, zinc oxide and indium tin oxide.

10. The apparatus according to claim 9, wherein a short wavelength filtering material is coated at the other side relative to the transparent conductive film and is configured to filter non-specific light.

11. The apparatus according to claim 1, wherein the reagent container is fixed into the accommodation space at an angle substantially perpendicular along the first perforation and contacts the film upper surface of the glass through the second perforation and the retaining groove.

12. The apparatus according to claim 1, wherein the number of the accommodation space is substantially equal to the number of the reagent container, and the height of any accommodation space is substantially the same as the reactants and reagents loaded in the reagent container, wherein the accommodation space is configured to avoid the reagent container from external temperature disturbance when PCR or RT-PCR is performed.

13. An apparatus with a reagent container for performing PCR or RT-PCR by thermal convection, and said reagent container has reactants and reagents, wherein the apparatus comprises:

(1) a first bracket, disposed on a horizontal plane, wherein the first bracket comprises a first perforation;

(2) a second bracket, disposed below the first bracket and substantially parallel to the horizontal plane, wherein the second bracket comprises a second perforation, and the second bracket has a bracket upper surface and a bracket lower surface, wherein the bracket lower surface of the second bracket further includes a retaining groove, the retaining groove is substantially parallel to the horizontal plane and connects the second perforation;

(3) a temperature sensing device, disposed in the retaining groove, wherein the temperature sensing device comprises a glass, a temperature sensor and a contact node, wherein the glass has a film upper surface and a film lower surface, and a transparent conductive film is disposed on the film upper surface or the film lower surface, the size of the glass is substantially equal to the size of the retaining groove so the glass can be fixed into the retaining groove by the film upper surface or the film lower surface, the contact node is disposed at the same side of the transparent conductive film, the temperature sensor is disposed on the film upper surface or the film lower surface and is configured to measure a temperature of the transparent conductive film;

(4) a power supplying device, comprising a power supply and a power regulator, wherein the power supply supplies power to the contact node so the temperature sensing device can perform a heat process, and the power regulator is configured to control an output current;

(5) an accommodation space, disposed between the first bracket and the second bracket and is configured to accommodate the reagent container, wherein the reagent container is placed into the accommodation space through the first perforation and further through the second perforation and the retaining groove to contact the film upper surface of the glass; and (6) a processor, for controlling the power regulator, and receiving signals from the temperature sensor to control the temperature sensor, wherein, when the transparent conductive film reaches a predetermined value, a temperature of the transparent conductive film is reported back to the processor by the temperature sensor, and the processer controls the power regulator not to supply the power.

14. The apparatus according to claim 13, wherein the apparatus is applied to PCR or RT-PCR.

15. The apparatus according to claim 13, wherein the transparent conductive film coated on the glass comprises tin oxide, indium oxide, zinc oxide or indium tin oxide.

16. The apparatus according to claim 13, wherein the reagent container is fixed into the accommodation space at an angle substantially perpendicular along the first perforation and contacts the film upper surface of the glass through the second perforation and the retaining groove.

17. The apparatus according to claim 13, wherein the number of the accommodation space is substantially equal to the number of the reagent container, and the height of any accommodation space is substantially the same as the reactants and reagents loaded in the reagent container wherein the accommodation space is configured to avoid the reagent container from external temperature disturbance when PCR or RT-PCR is performed.

* * * * *